United States Patent [19]
Avitall

[11] Patent Number: 5,441,483
[45] Date of Patent: Aug. 15, 1995

[54] CATHETER DEFLECTION CONTROL

[76] Inventor: Boaz Avitall, 4868 N. Ardmore Ave., Milwaukee, Wis. 53217

[21] Appl. No.: 148,598

[22] Filed: Nov. 8, 1993

Related U.S. Application Data

[63] Continuation-in-part of Ser. No. 976,784, Nov. 16, 1992, abandoned.

[51] Int. Cl.[6] .............................................. A61M 37/00
[52] U.S. Cl. ..................................................... 604/95
[58] Field of Search ................... 604/95, 280, 281, 282; 128/4, 6, 656-658, 786

[56] References Cited

U.S. PATENT DOCUMENTS

| | | | |
|---|---|---|---|
| 2,498,692 | 2/1950 | Mains | 128/348 |
| 3,266,059 | 8/1966 | Stelle | 3/12.3 |
| 3,470,876 | 10/1969 | Barchilon | 604/95 |
| 3,557,780 | 1/1971 | Sato | 128/4 |
| 3,605,725 | 9/1971 | Bentov | 128/4 |
| 4,353,358 | 10/1982 | Emerson | 128/4 |
| 4,580,551 | 4/1986 | Siegmund et al. | 128/4 |
| 4,718,419 | 1/1988 | Okada | 128/4 |
| 4,753,223 | 6/1988 | Bremer | 128/4 |
| 4,785,815 | 11/1988 | Cohen | 128/642 |
| 4,869,248 | 9/1989 | Narula | 128/303.13 |
| 4,873,965 | 10/1989 | Danieli | 128/6 |
| 4,911,148 | 3/1990 | Sosnowski et al. | 128/6 |
| 4,960,134 | 10/1990 | Webster, Jr. | 128/786 |
| 4,976,688 | 12/1990 | Rosenblum | 604/95 |
| 4,977,887 | 12/1990 | Gouda | 128/4 |
| 5,044,375 | 9/1991 | Bach, Jr. et al. | 128/786 |
| 5,098,412 | 3/1992 | Shiu | 604/280 |
| 5,176,126 | 1/1993 | Chikama | 128/4 |
| 5,228,442 | 7/1993 | Imran | 128/642 |
| 5,238,005 | 8/1993 | Imran | 604/96 |
| 5,318,526 | 6/1994 | Cohen | 604/95 |
| 5,383,852 | 1/1995 | Stevens-Wright | 604/95 |

FOREIGN PATENT DOCUMENTS

| | | | |
|---|---|---|---|
| 4510991 | 4/1967 | Japan | 128/4 |

*Primary Examiner*—C. Fred Rosenbaum
*Assistant Examiner*—Frank Wilkens, III
*Attorney, Agent, or Firm*—Haugen and Nikolai

[57] ABSTRACT

A vascular catheter with a distal working tip is provided with precise shape control. The tip section optionally includes a plurality of weakened segments of preferred deflection spaced from the distal end. Reciprocally operable control wires are attached distal each deflection segment and extend to a proximal control handle where they are attached to manual controls for adjusting longitudinal tension to the distal section of the catheter from just beyond the deflection segments in a manner that encourages bending or collapse of the deflection segments in the direction of the weakened or cutout areas. An additional reciprocating adjustable deflection shape control element, preferably a rod or tubular member which itself optionally may have areas of preferred deflection slidably reciprocates slidably within the main internal lumen of the working catheter section, and may be axially adjusted in relation to the working catheter segment to precisely modify the deflection characteristics of the catheter section sought to be controlled as produced by the control wires.

61 Claims, 11 Drawing Sheets

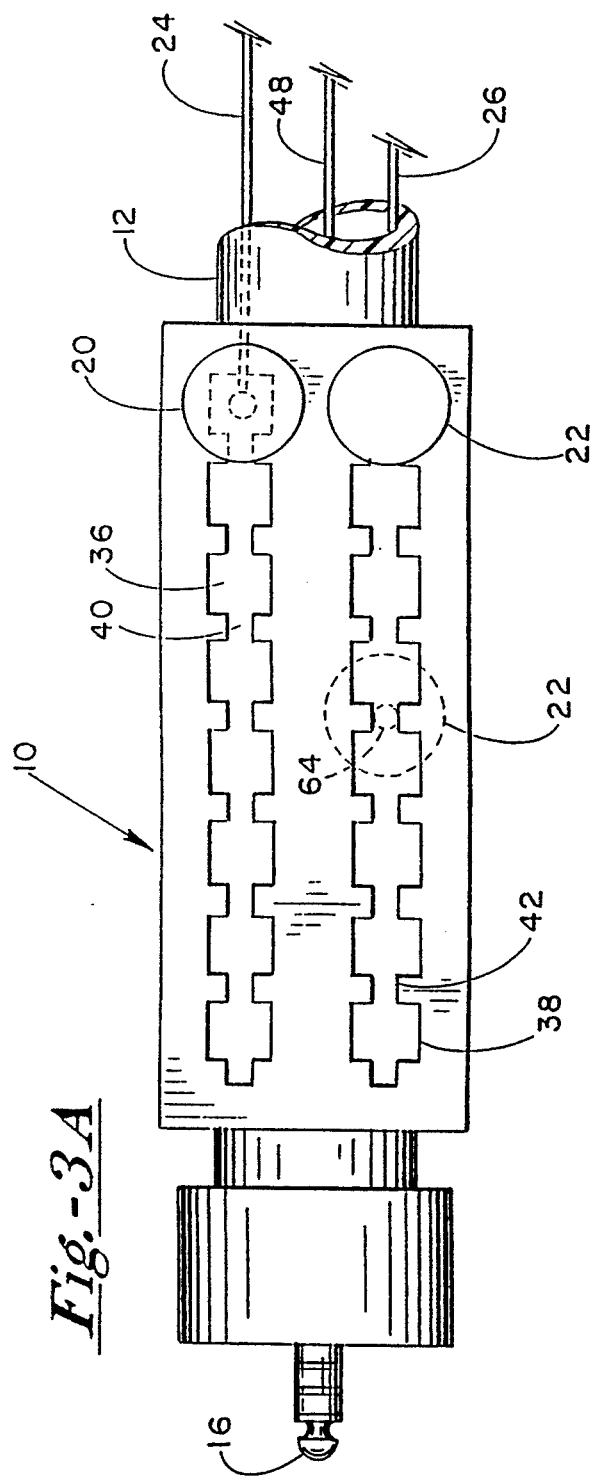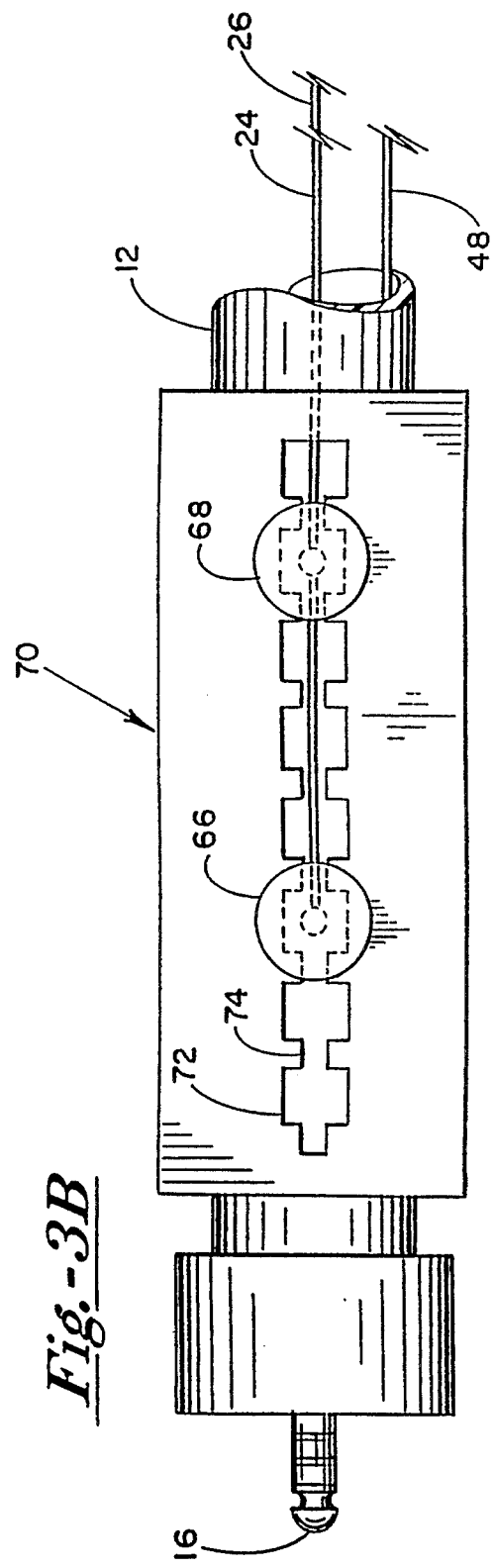
Fig.-3A
Fig.-3B

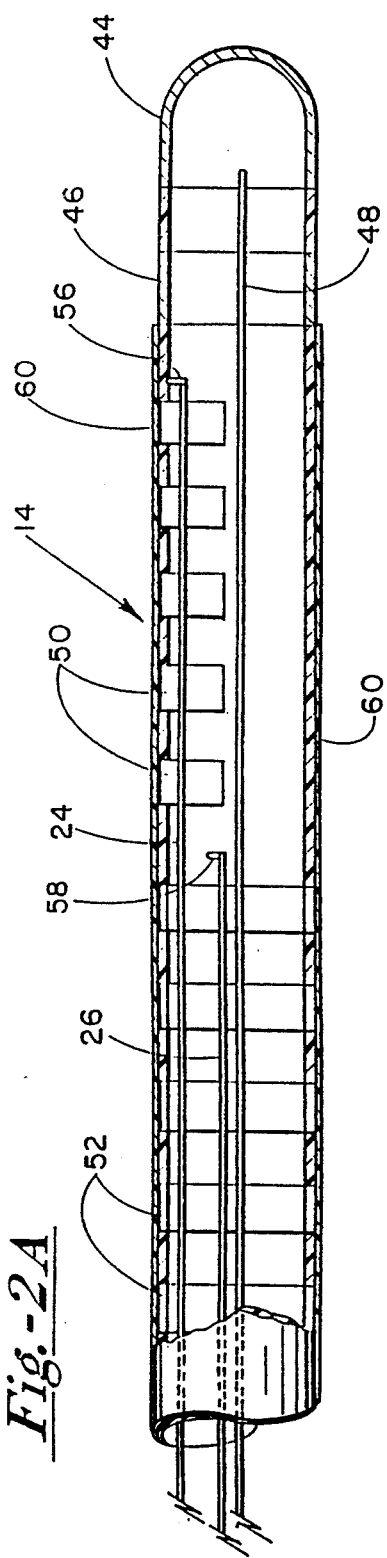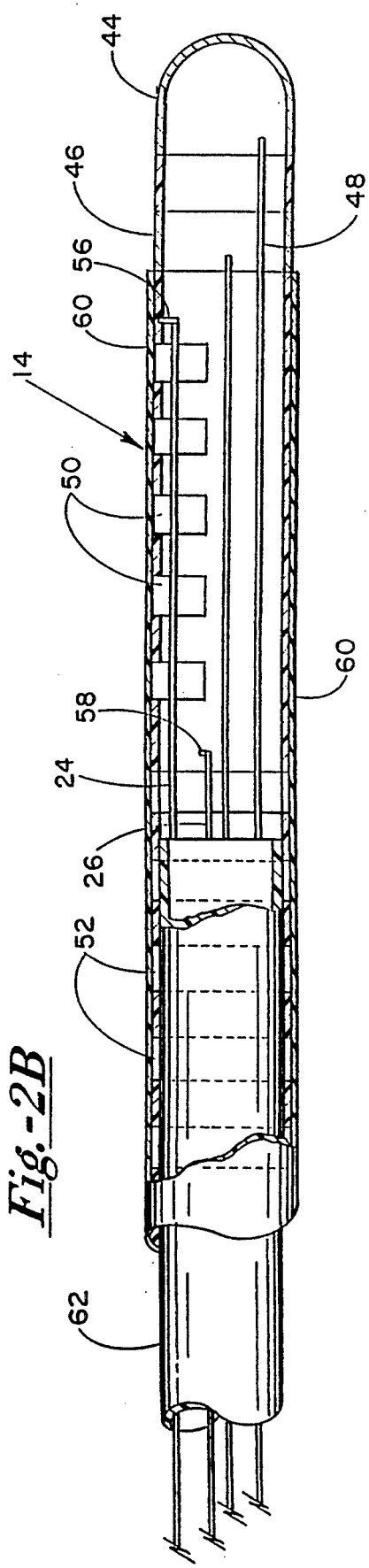

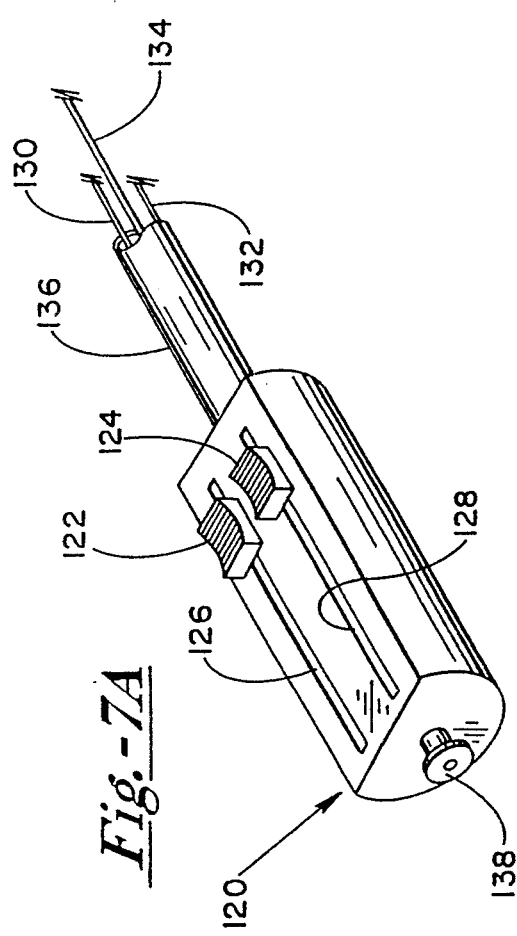
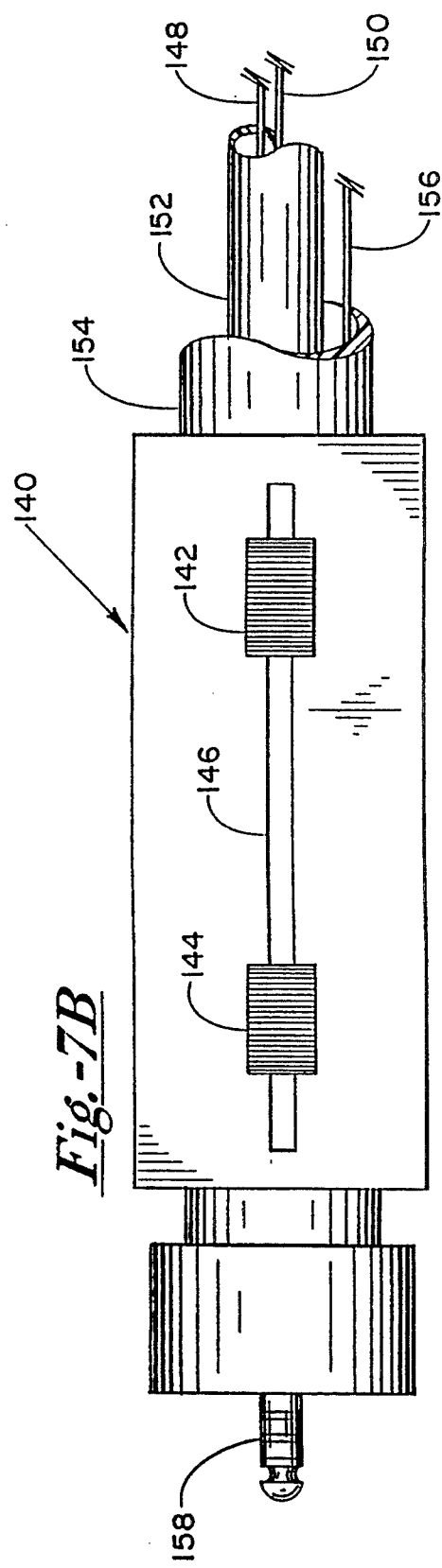

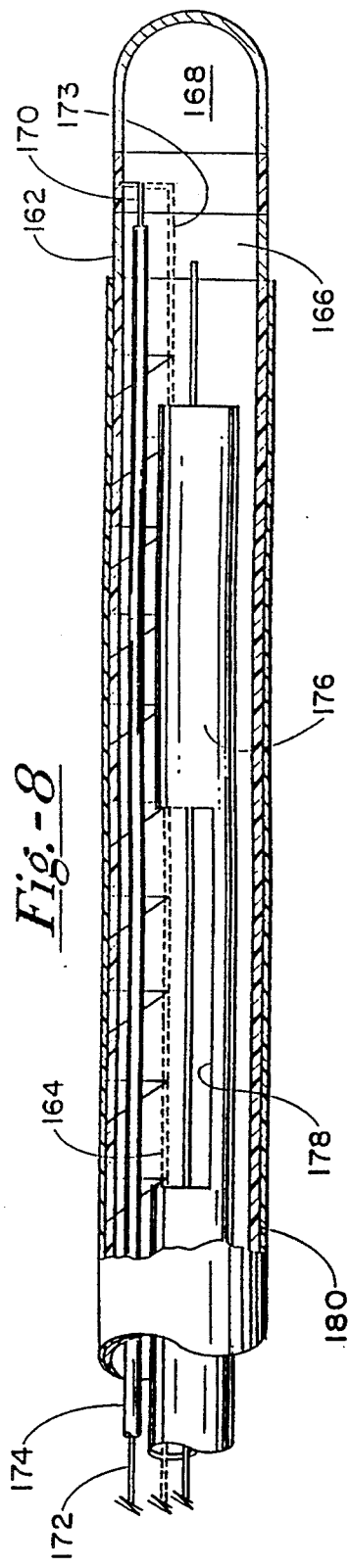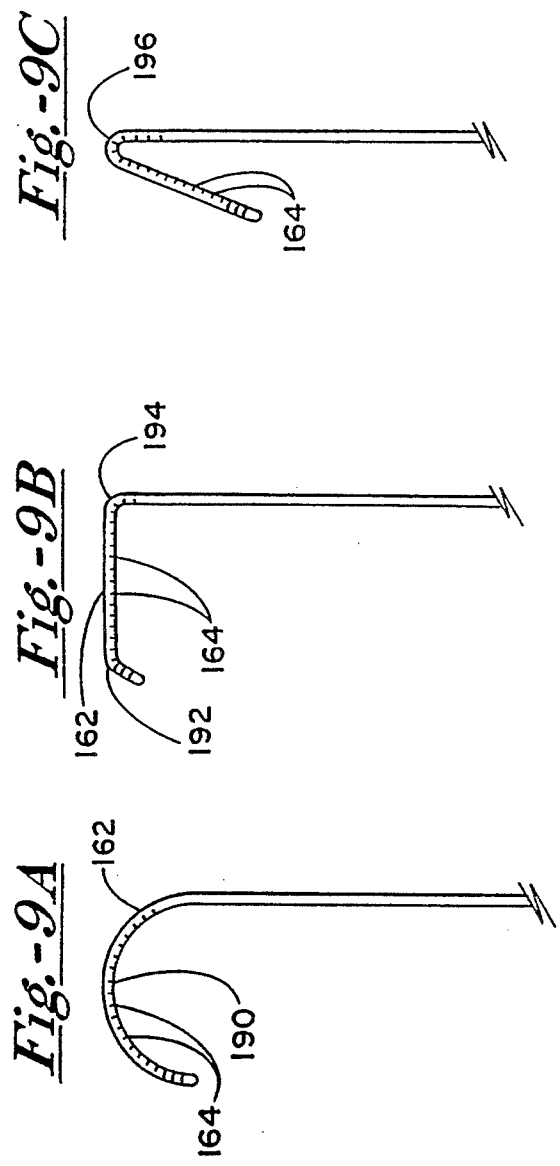

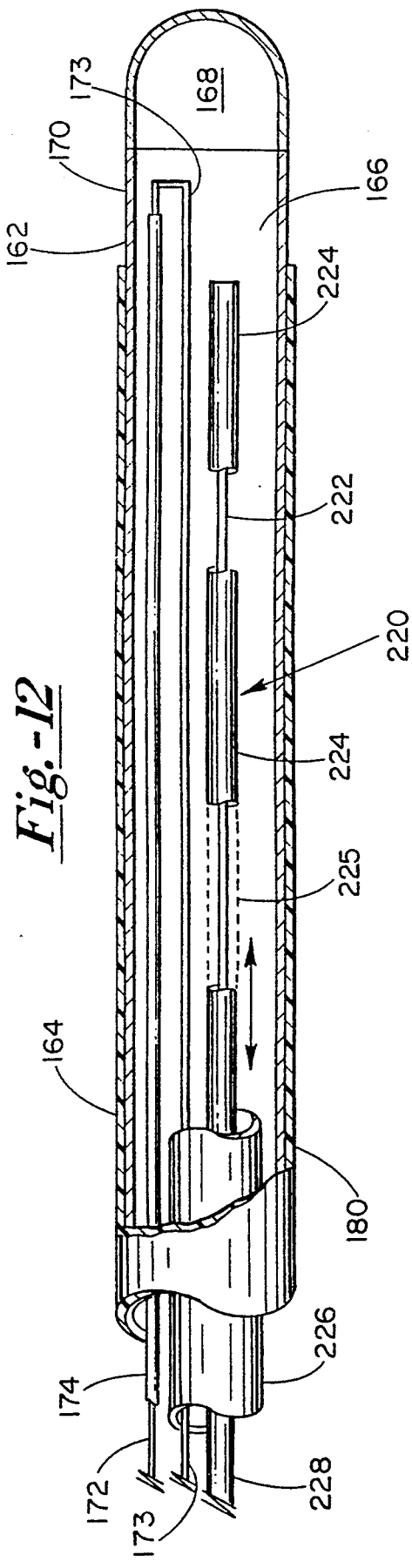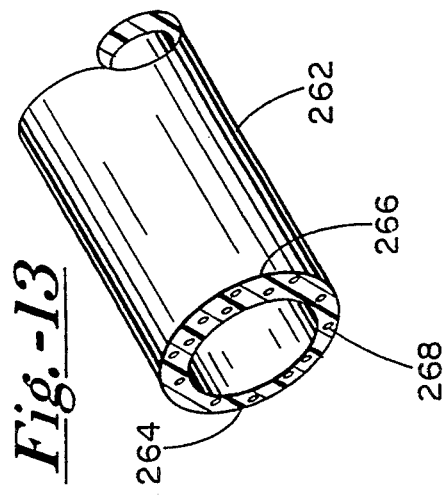

CATHETER DEFLECTION CONTROL

CROSS-REFERENCE TO RELATED APPLICATIONS

This application is a continuation-in-part of application Ser. No. 07/976,784, which was filed Nov. 16, 1992, now abandoned. Reference is further made to patent application Ser. No. 07/909,867 which was filed Jul. 7, 1992, which is a continuation-in-part of co-pending application Ser. No. 07/835,553 filed Feb. 14, 1992. Reference is further made to application Ser. No. 07/909,869 filed Jul. 7, 1992, which is a continuation-in-part of co-pending application Ser. No. 07/840,162 filed Feb. 24, 1992; and to application Ser. No. 07/840,026 filed Feb. 24, 1992. These cross-referenced applications share a common inventorship with that of the present application and all relate to improved vascular catheters of a class having controlled flexible distal tips.

BACKGROUND OF THE INVENTION

I. Field of the Invention

The present invention is directed generally to mechanical improvements in vascular catheters that has wide application. The invention applies to catheters of a type usable by cardiologists for peripheral or coronary catheterization or balloon angioplasty, embraces catheters used by electrophysiologists for performing electrical mapping of the heart or electrical tissue ablation and also involves devices used by radiologists in cerebral or any arteriography/venography procedures or cavitary visualizations or intervention. In particular, the invention endows such catheters with sharp-angle, multi-directional deflection capabilities which enables them to access and treat hard-to-reach areas such as branching vessels, or the like. The invention, in some cases, may eliminate the need for a guidewire and the time required to perform procedures such as electrical mapping to identify the source of cardiac arrhythmia may be greatly shortened and more successfully accomplished owing to the improved maneuverability of the catheter.

II. Discussion of the Related Art

Electrical mapping to discover the source of cardiac arrhythmias and subsequent electrical tissue ablation to eliminate such sources represents one important application for the improved catheters of the present invention. In addition, the heart chambers, valves and associated vessels represent a true challenge with respect to the intricacy of maneuvering therethrough and reaching remote areas and surfaces for mapping and ablation.

Normal cardiac pacing, in a healthy heart, is controlled by a special structure known as the sinoatrial node (SA node). This is the natural pacemaker of the heart and is a specialized tissue located within the muscle walls of the right atrium. The SA node provides impulses which dominate the inherent or natural rhythmic contractions of the heart atria and the ventricles. This dominance or control involves the transmission of ionic impulses through cardiac conduction pathways in the atria and the ventricles which cause the heart to contract and relax in an orderly sequence at a rate dictated by the SA node. This sequence ensures that blood flow to the systemic circulation or the pulmonary system will be maximized with each ventricular contraction. The SA node has its own inherent rate which can be modified by signals from the nervous system. In response to excitement, physical activity, etc., the sympathetic and parasympathetic nervous systems react to modify the rate.

A depolarization impulse begins with the SA node and spreads as an electrical wave from its location in the right atrium across to the left atrium and down toward the transition zone between the atrium and the ventricles where another node, known as the atrioventricular (A-V) node or junction, is located. This impulse conducts through the A-V node in a slower fashion and continues to a common pathway known as the Bundle of His between the right and left ventricles, then into multiple paths called right and left bundle branches, each bundle branch supplying one ventricle. These bundle branches then divide into an extensive network of finer paths of conducting tissue which spread from the inner to the outer surfaces of the heart and which are referred to as the Purkinje fibers. These fibers feed the depolarization impulse into all portions of the ventricular myocardium.

As long as this system is intact, impulses are transmitted normally and cardiac rhythm is maintained. The natural impulse or current flow in the cardiac conduction system, however, may be interrupted or altered by congenital defect, disease or injury which can cause the formation of scar tissue. When a sufficiently severe injury or a congenital defect is present in the cardiac conductive pathways or in the ventricular myocardium, the electrical impulses are not transmitted normally and rhythmic disturbances known as cardiac arrhythmias can occur. With respect to such disturbances, the term bradycardia is used to describe an abnormal slowing of the cardiac contractions and the term tachycardia is used to describe abnormally rapid heart action. While either of these conditions can endanger the life of the patient, tachycardia is more serious, particularly in patients having underlying heart disease.

Ventricular tachycardia and other ventricular arrhythmias have been treated with a number of drugs such as lidocaine, quinidine and procainamide. In cases of excessive sympathetic nervous activity or adrenal secretion, Beta blocking drugs have been used. In cases where drug therapy has been ineffective in preventing tachyarrhythmias, certain surgical procedures have been used to ablate the arrhythmogenic tissue either from the atrium or the ventricles. This procedure involves major surgery in which an incision through the pericardium and heart muscle is made locate the arrhythmogenic tissue, which is then frozen or surgically removed to be replaced by scar tissue.

Because open-heart surgery is a high risk procedure which requires a prolonged period of hospitalization and recuperation, a less traumatic solution is needed. In response, catheters of various types have been devised and used for diagnosing and treating a number of cardiac abnormalities to avoid the trauma of open-heart surgery. For example, as a method for resolving atherosclerotic plaque build up, stenotic lesions are now routinely opened by the use of balloon angioplasty. In this procedure, a balloon carrying catheter is navigated through the patient's vascular system to the location of the stenosis. The balloon is inflated by fluid injected through a lumen of the catheter to apply pressure to the walls of the clogged vessel, thereby opening it. Angioplasty catheterization may require sophisticated intricate vascular navigation in which acute angle catheters definitely would be advantageous.

Catheter devices have also been used to locate and ablate cardiac conduction pathways. One such device is shown in U.S. Pat. No. 4,785,815, in which a catheter tube carries at its distal end at least one electrode for sensing membrane potentials within the heart, together with a heating device used to thermally ablate at least a portion of the pathway located by the sensing device. Another thermal ablation catheter for microtransection or macrotransection of conduction pathways within the heart, which uses a resistive heating element at its distal end for highly localized treatment, is illustrated and described in U.S. Pat. No. 4,869,248. These devices are generally effective once the ablating element is properly positioned at the localized area of interest. A catheter device tip of the class described has also been developed which employs a single handle operated deflection wire control system. Such a device is disclosed in U.S. Pat. No. 4,960,134. U.S. Pat. No. 4,911,148 discloses a device in which a series of aligned spaced cutouts are provided in distal section the multi-lumen plastic tube of an optical endoscopic device together with a tensioning draw wire to facilitate unidirectional deflection of the distal tip portion of the endoscopic device. This system, however, is also limited to unidirectional deflection.

The application of electrophysiological catheter ablation procedures, for example, often is hampered by the inability of the operator to maneuver the catheter tip to the precise location of the arrhythmogenic tissue. This is primarily a result of the limited maneuverability of the catheter tube itself. The catheter tube must have sufficient strength and stiffness to be guided through the vascular system to the vicinity of the tissue of interest. This construction does not allow the degree of flexibility at the tip of the catheter needed to perform intricate multi-directional manipulations in the highly localized areas involved. Available catheters, even catheters with single deflection wire control, are characterized by inadequate control of fine movements and have tips that can be deflected only in planes parallel to the main catheter tube. They lack the ability for controlled lateral movement in other directions within the atria or the ventricles.

Most present cardiac tissue ablation procedures involve the use of radio frequency (RF) electrical current transmitted to the tissue via a catheter which is positioned as closely as possible to the arrhythmogenic site within the atria or ventricles. Radio frequency electrical current heats the tissue surrounding the catheter, creating a discrete dense lesion. In order for the patient to be cured of the arrhythmia, the lesion must be created in the area from which the arrhythmia originates. Improvement in the maneuverability of such devices could optimize precise positioning of the catheter prior to ablation.

Additional applications for highly maneuverable, multi-directional deflectable devices abound. They include peripheral or coronary catheterization or balloon angioplasty and anglographical applications.

SUMMARY OF THE INVENTION

The present invention provides a new design which endows the catheter tip with greatly increased multi-directional sharp-angle flexibility. This affords the catheter an amount of "fine tuning" by providing improved intricate or sophisticated maneuverability enabling catheter use in hard-to-reach branching vessels for mapping remote organ surfaces, or facilitates accessing certain chamber surfaces or valve surface areas in the heart. This is accomplished by the provision of any of several unique catheter/sheath constructions which allow independent radical deflection of one or more longitudinally spaced or abutting shaft deflection segments disposed in the same or different directions at the behest of associated control wires.

In accordance with one embodiment of the present invention, two or more radially and longitudinally spaced deflection segments each having a plurality of aligned, longitudinally spaced, essentially parallel transverse weakened areas are provided to facilitate deflection or collapse in the direction of the weakened areas upon the application of a longitudinal contractive force from a point distal of the series of weakened areas or areas to be deflected. Two or more of these deflection segments may be serially located in radial diversity to produce multi-directional deflection capability. Independent tensioning devices in the form of tensionable reciprocating control wires fixed in the catheter wall just above each deflection segment (or at least above) the most distal deflection segment control deflection. The longitudinal axis of the catheter or sheath is predisposed to bend or collapse laterally in the direction of the notches of each of the deflector segments in response to the application of tension in the reciprocating draw or pull control wire.

The weakened areas in the deflection segments may take any convenient form but are illustrated in the detailed description generally in the form of notches or cutouts in the catheter wall spaced along the side of the sheath or catheter shell and extending laterally or transversely about one-fourth to one-half of the circumference of the sheath or catheter in an aligned manner the weakened areas of a given deflection segment being preferably of similar radial disposition. The draw or pull wire is capable of two directional longitudinal or reciprocal displacements within the catheter and has a distal end attached to the catheter wall aligned with and just above each series of notches.

Additional deflection segments each containing a series of aligned notches or weakened areas can be provided at the same or varying radial angles and axial distances depending on the desired variations in multi-directional deflection shapes desired. Deflection is controlled by a reciprocating pull or draw wire preferably attached just above each deflection segment to urge the shaft to bend in the direction of the notches under the tension control of that draw wire. Of course, a more distally attached draw wire will produce deflection in all deflection segments proximal the point of attachment of the draw wire. The relative stiffness of the parts is preferably such that re-extending the wire will reduce the deflection or produce a straightening of the catheter. Extreme flexibility and fine directional control is achieved by adjusting the tension in a plurality of draw wires or one distal draw wire in accordance with the desired deflection or shape of catheter tip required. This allows controlled contortions for intricate manipulation at a level of multi-directional flexibility not heretofore available.

The catheter wall or sheath also can be provided with one or more asymmetrical wall segments spaced lengthwise of the distal section having a thin or weak direction. Pull wires are attached just above the thin or weak segments. The weak or thin segments act as deflection segments much in the fashion of the notches.

In an alternate embodiment, one or more deflection segments in the main catheter are combined with a longitudinally displaceable adjustable inner or outer catheter or sheath device which slides over or inside a main lumen of the deflectable catheter or sheath to increase rigidity by limiting deflection of the weakened areas and so further cooperate with and further modify the effect of the deflection of the distal portion of the device when adjusted reciprocally with respect to the deflection segment.

In a further embodiment, an inner deflection guide catheter is provided capable of controlled reciprocal motion in the lumen of the main catheter and which itself has longitudinally spaced weakened areas, which may be extended cut-out portions. The cutout portions enable the inner deflection guide tube to flex with the outer catheter in these limited areas. The deflection control wire is connected to the outer catheter above the deflection segment. Deflection of the outer catheter is thus controlled by the relative longitudinal placement of the cutout of the inner catheter.

In yet another embodiment, an axially adjustable flexure control shaft of modulated flexure is provided instead of the inner deflection guide catheter to control the points of flexure of the deflection of the main catheter. This may be in the form of a resilient member of constant or varying bend resistance or diameter such as a wire member that readily deflects in a certain area or areas and springs back when the bending force is released. The varying diameter or resistance to bending may be omnidirectional or made direction specific with regard to deflection. The deflection shaft or wire can be contained in an internal catheter lumen.

The cuts in the sheath or catheter that provide the increased flexibility are covered as with a thin polymeric ply of, e.g., polyurethane, shroud material to protect the integrity of the catheter lumen in the case of a sheath and over the outer surface of the catheter itself in the case of an ablation device. Such covering is not necessary for extruded catheters having weakened areas or reinforced stronger areas to create a deflection differential. This lining material is very thin, impermeable to liquids, flexible and quite strong allowing the shaft to flex as desired without significant impediment. The detailed character of the deflection ability of the system may be determined specifically according to the particular embodiment and application and requirements contemplated.

In one successful embodiment, two or more radially diverse series of aligned, longitudinally spaced transverse notches are provided in the working catheter tube spaced just proximal of the distal end thereof. Reciprocating pull or draw wires are provided having distal ends attached to the sidewall of the catheter just above each series of notches. The pull or draw wires are threaded through a channel in the wall of the catheter or sheath exiting the shaft on the side into a control handle. Each wire is attached to the shaft of a sliding control button. The button is also provided with a spring biased latching mechanism in which depression of the button allows it to be movable along a channel provided with a series of spaced shaped positive stop positions into which the lower shaft of the button, which has a matching shape, may be directed by a return spring when pressure is released from the button.

Other types of deflection and tension control mechanisms are contemplated including the use of a control handle having a sliding knob which can be tightened in place as by a set screw. Shafts which rotate and wind or unwind the pull wire in the manner of a reel are also contemplated.

BRIEF DESCRIPTION OF THE DRAWINGS

In the drawings wherein like numerals are utilized to designate like parts throughout the same:

FIG. 2A is a greatly enlarged sectional view of the distal section of the catheter of FIG. 1A in an undeflected state;

FIG. 2B is a cross sectional view of an alternate embodiment to that of FIG. 2A;

FIGS. 3A and 3B are enlarged views of control handles usable with the catheter of FIG. 1A;

FIG. 7A is a broken perspective view of an alternate handle to those shown in FIGS. 3A and 3B;

FIG. 7B is a broken plan view of another alternate handle for a deflection catheter;

FIG. 8 depicts a broken distal fragmentary side view, partially in section, of a deflection catheter having a deflection guide inner catheter tube;

FIGS. 9A–9C are schematic representations of deflection patterns of the catheter of FIG. 8;

FIG. 12 is a view similar to FIG. 8 using a variable diameter deflection guide member; and FIG. 13 is a fragmentary representation of a catheter tube as used in the invention showing an asymmetric wall segment.

DETAILED DESCRIPTION

A most important aspect of the present invention is to afford enhanced single- or multi-directional flexibility to distal sections of catheter systems of a class which are used for procedures which require controlled intricate maneuvering of or tortuous paths to be described by the distal tip to succeed. Applications include the use of catheters to electrically map or ablate difficult to access areas of organ tissue and addressing difficult to access sites of vascular stenoses. The catheters of the invention can take any of several forms or embodiments, any of which might be preferred for a particular application or procedure. The several drawing figures illustrate the principles of the invention but are by no means intended to limit or exhaust the contemplated embodiments.

Figure 1A:
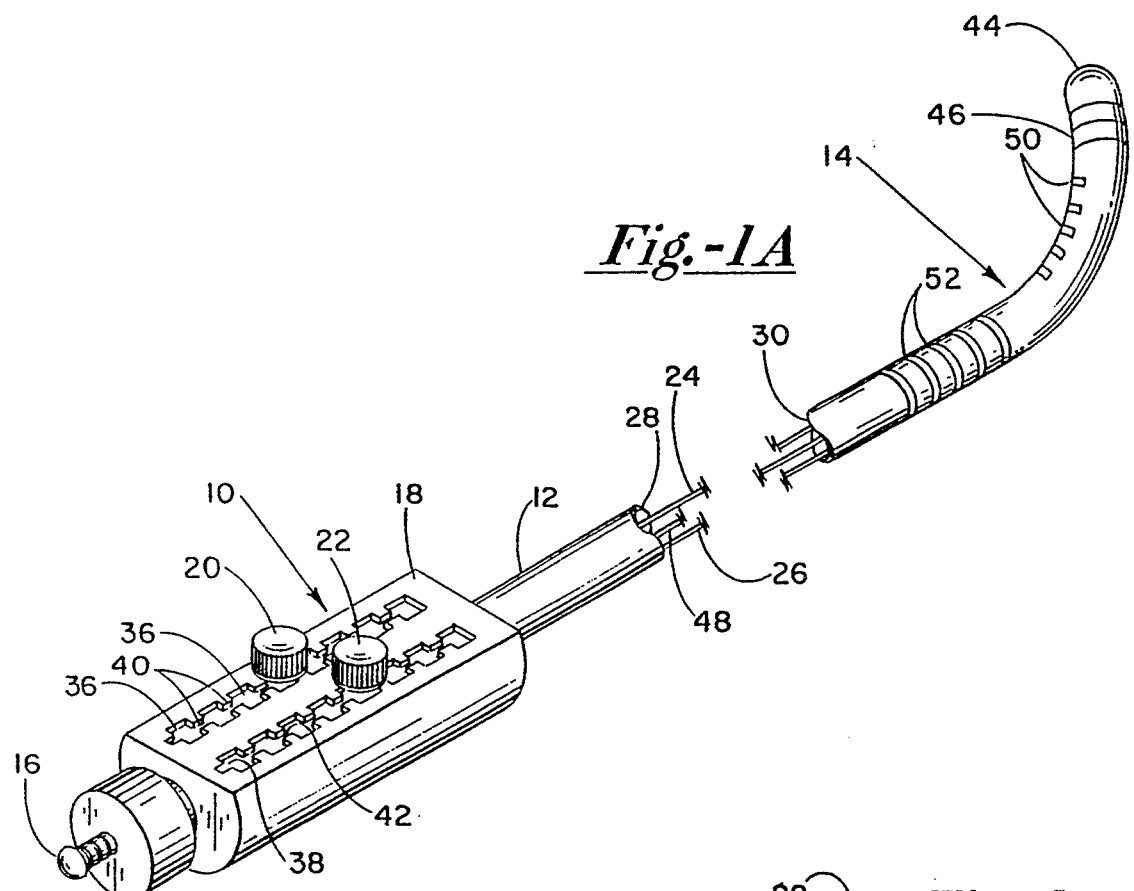
FIG. 1A represents an enlarged broken perspective view with parts broken away of a multi-direction deflectable catheter system in accordance with the invention.

FIG. 1A depicts a typical catheter of a class being particularly adapted for mapping electrical activity of tissue and for accurate thermal tissue ablation. The catheter has a handle portion shown generally at 10, a central, relatively rigid tubular section 12, and a flexible distal maneuverable tip section 14. The central section 12 is shown broken as it depicts the long main body of the catheter which navigates the vascular system from the point of insertion to a point close to the site which the tip section 14 is designed to address.

The handle portion of the ablation device further includes an electrical jack-type, plug-in device shown at 16 but which provides external connections for multiple input/output electrical conductors, and connections for any other type of input/output devices associated with the operation of the catheter. These are well-known in the art and, for example, material in any of the above-referenced co-pending applications may be consulted and deemed incorporated herein for such details as are not fully provided in this application.

Deflection control devices are centrally located in the handle portion 10 and include a pair of longitudinally adjustable tension control buttons or knurled knobs as at 20 and 22 which are respectively connected to a pair of tensioning, pull or draw wires 24 and 26, respectively. The draw wires, in turn, extend from the control assembly through the main lumen 28 of the central tubular section 12 and the main lumen 30 of the distal tubular section 14 and thereafter are attached to the inner catheter wall as at 56 and 58 (FIGS. 2A and 2B). The top outer shell 18 of the hand grip 10 of the tension control system further contains a pair of channels describing respective series of longitudinally spaced shaped openings, possibly rectangles as at 36 and 38, separated by short, narrow channel segments as at 40 and 42.

The flexible distal catheter segment 14 itself may be constructed according to known catheter technology and practice and so may typically consist of a segment of a length of 3 to 30 cm of flexible reinforced polymer tubing of benign chemistry having an outside diameter of 4 F or more depending on the application. An electrode-containing platinum catheter tip system with tip electrode 44 is provided in the case of an electrical mapping/ablation device, and one or more additional spaced parallel ring electrodes as at 46. The tip electrode 44 and electrode 46 are connected electrically to input/output devices external to the catheter via an electrical connecting wire bundle illustrated at 48.

A pair of end or distal deflection segments are depicted just proximal of the electrode 46 and each includes a series of five (5) spaced parallel lateral cuts in the form of discrete aligned notches 50 and 52 which may be any desired length or shape, such as triangular or trapezoidal in shape, but generally subtend a radial angle from approximately 90 to 180 degrees of the 360° circumference of the catheter tube 14 (FIG. 1B) and are trapezoidal in shape and may appear as cutouts or notches in the catheter tube 14. The second set of cuts 52, provided proximal to the distal set 50, may address a radially diverse direction rotated an amount from the cuts 48 and comprise a proximal deflection segment in the flexible tip of the catheter portion 14.

Figure 11A:
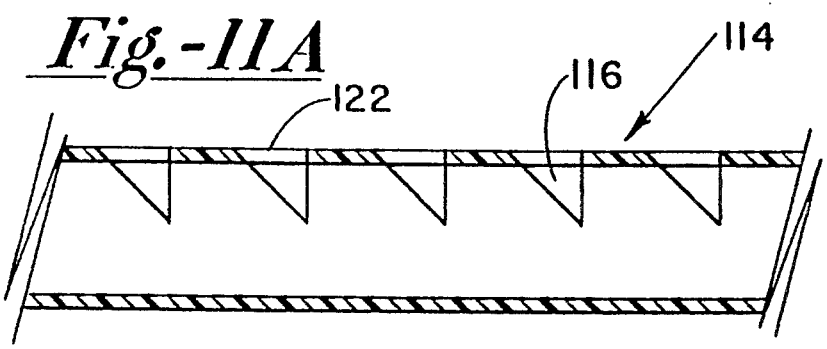
FIGS. 11A–11C are fragmentary views illustrating alternate notch or cutout shapes usable with any catheter.
Figure 11B:
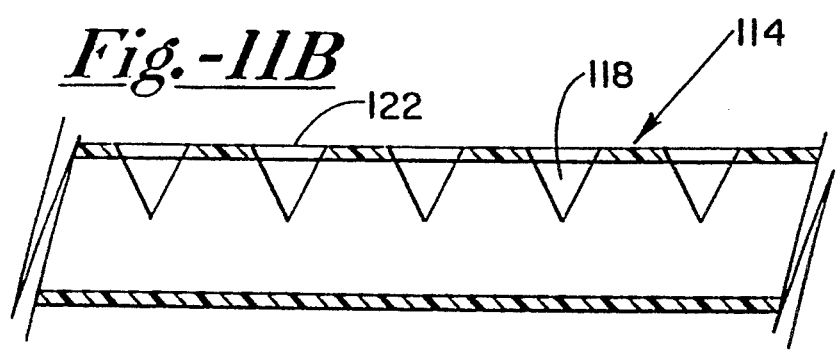
Figure 11C:
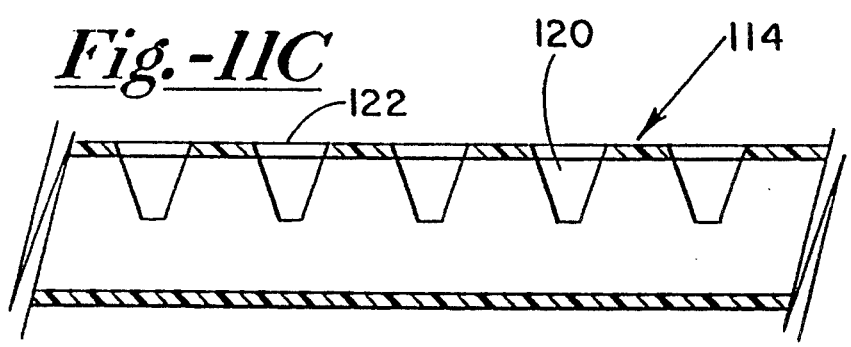

The illustrated combination (FIG. 1B) provides dual directioned deflection. The cutouts 50 or 52 may be in the shape of notches of any desired width or shape and depth (or angle subtended). The number of such openings in a deflection segment can be varied in accordance with the materials of catheter construction, use and flexure requirements of the system. Additional shapes are illustrated in FIGS. 11A–11C in which distal catheter fragments 114 are shown to illustrate deflection segments with triangular cutouts at 116 and 118 and trapezoids at 120. The sheath or outer protective membrane 122 covers the openings. Of course, additional deflection segments at still different or even the same angle dispositions may be employed in the device, the number and disposition being a matter of desired application.

A portion of the flexible tip section of the catheter is illustrated in the enlarged sectional view of FIG. 2A. The pull or draw control wires 24 and 26 are permanently attached to the inner wall 54 of the catheter segment 14 as by respective T members 56 and 58. Each control wire is attached just distal of a respective deflection segment, preferably midway of the notches. A further thin outer membrane or lining material 60, impermeable to liquids, flexible and quite strong, is provided which allows the catheter shaft 14 to flex in accordance with the deflection segments utilizing the notches illustrated yet which preserves the liquid-tight integrity of the interior lumen 30 with respect to the external ambient surroundings. The membrane covers all the deflection segments of the distal catheter section 14.

In accordance with the invention, the degree of deflection or contortion achieved may vary greatly. This in part is determined by the number, size, direction, shape and spacing of cuts in the series making up a given deflection segment. Considerations include how wide the aligned cuts are made, i.e., amount of notching, and the number and angular relationship of the various segments or groups of cuts. The distance between the deflection segments, defined by the distance between the groups of aligned cuts, also affects the deflection characteristics. This phenomenon can also be controlled by using the auxiliary or deflection control sheath or by making the proximal shaft segments somewhat less flexible compared to the distal shaft as the shaft progresses through the multiple series of deflection segments.

One important aspect of the invention involves control of the multi-directional deflection of the flexible distal tip section of the catheter. Accordingly, FIG. 2B depicts the embodiment of FIG. 2A further provided with an additional flexure modulating device in the form of an internal catheter tube 62 reciprocally slidably mounted inside the catheter 14. The inner catheter member 62 cooperates with the catheter 14 to modify the local deflection or flexure characteristic of the flexible tip section as it is advanced to and beyond one or more openings or cutouts 52 and 50. The member 62 is preferably rigid, or at least more difficult to flex than the notched outer catheter 14. As is the case with the catheter 14, however, the member 62 may be endowed with any desired degree of rigidity or Shore hardness and is cooperatively coordinated with the tensioning of the draw wires 24 and 26 (described in greater detail below) to produce greater precision in flexure control. While it is preferred to locate the member 62 within the main lumen of the working catheter tip section 14, a slipover outer sheath may also be used.

FIG. 3A illustrates one handle tension adjusting mechanism showing a plurality of positions for each of the buttons or handles connected to the control wires, the longitudinal tension of which is to be adjusted. One of the handle devices 22 is shown superimposed in one location and in phantom at another with its respective stem or axle 64 in a position intermediate adjacent stops 36. An alternative embodiment is shown in FIG. 3B in which the knobs 66 and 68 are longitudinally aligned in a single slot or coaxial version of handle 10 at 70 further containing stops 72 and intermediate positions 74. The illustrated handles, of course, are but some of many similar and mechanically equivalent forms which can be used to adjust the tension in the wires and thereafter maintain the adjusted tension.

Figure 1B:
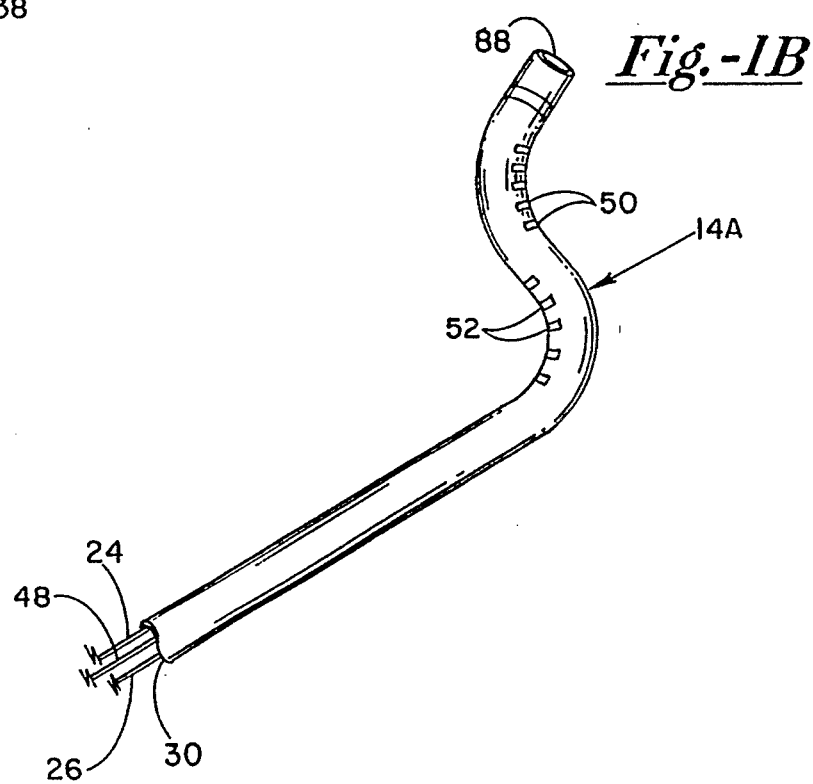
FIG. 1B is a fragmentary view showing bi-directional deflection of the catheter of FIG. 1A.
Figure 5A:
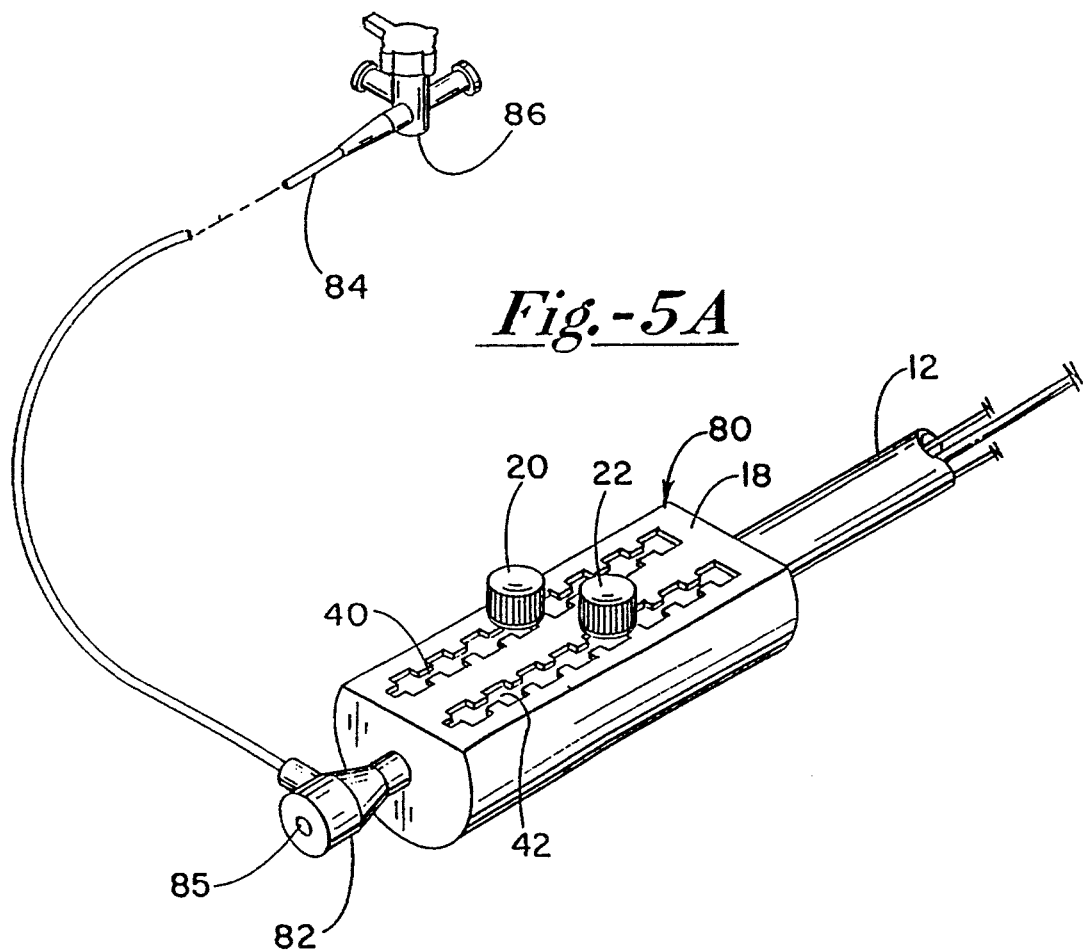
FIGS. 5A and 5B depict alternate handles for sheath type catheters.
Figure 5B:
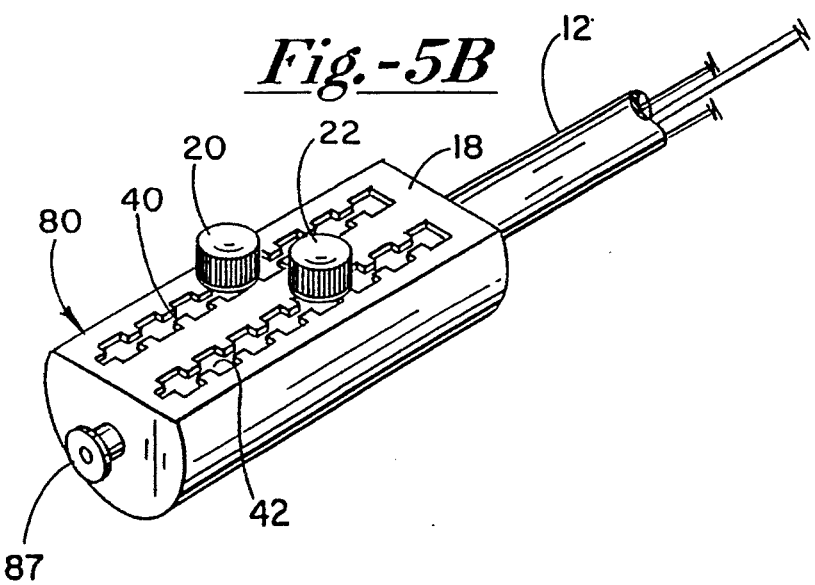

FIGS. 5A and 5B illustrate the handle of FIG. 1A as a sheath connected system with a sealed inlet rather than an ablation system. The handle 80 includes the same flexure controls and has a sealed inlet connection 82 with side tube 84 connecting a multi-position valve or stopcock 86. A further sealed access is shown at 85, and an alternative access is illustrated in FIG. 5B at 87. The system includes one or more open lumens extending to the flexible tip section 14 in a well-known manner as at 88 (FIG. 1B).

Figure 4A:
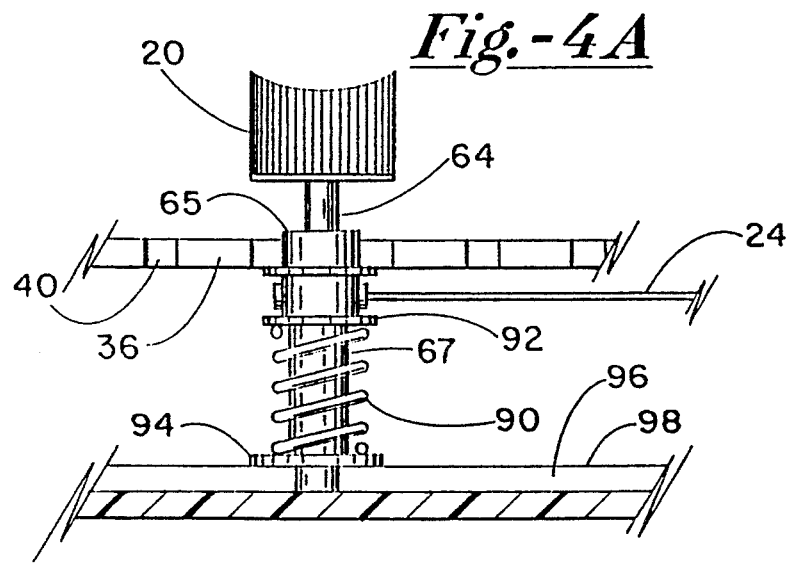
FIGS. 4A, 4B and 4C depict enlarged fragmentary details of an adjustable draw wire control button or handle in the locked and unlocked positions.
Figure 4B:
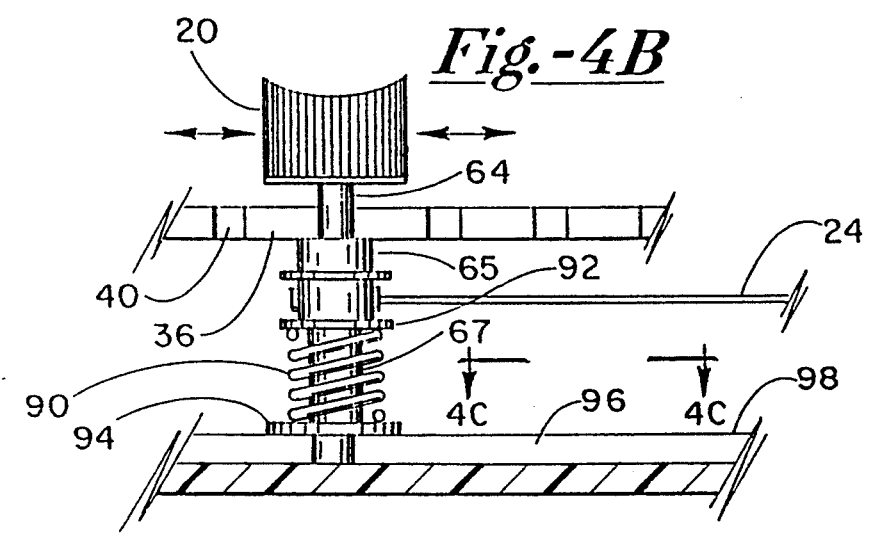
Figure 4C:
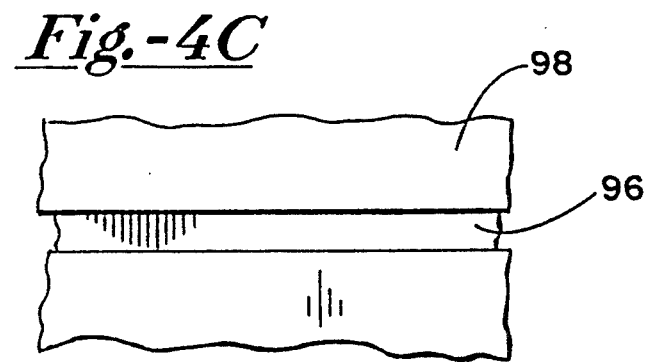

Mechanically, the buttons or knurled knobs as at 20, 22, 66 or 68, etc., may take any of several forms as might occur to those skilled in the art. These include a spring-loaded version illustrated in the locked and unlocked position in the enlarged fragmentary details of FIGS. 4A–4C and an alternate threaded embodiment shown in FIG. 6A–6D. The embodiment illustrated in FIGS. 4, 5A and 5B represent either operating handle as at 10 in FIGS. 1 and 3A and 70 in FIG. 3B. The alternate passages in top locations 40 and 42 are illustrated with respect to the locked and unlocked positions of FIGS. 4 and 5A, respectively. In FIG. 4, the top enclosure wall 18 of the handle member is shown, the top illustrating the stops and passages 40 and 42 on the bottom in section. The operating knob 22 is connected by a section of relatively thin stem 64 which, in turn, is connected to a relatively larger diameter hollow stem segment 65. This is followed by a segment of intermediate thickness 67 surrounded by a compression spring 90 flanked by spaced spring stops 92 and 94. The stem segment 67 is designed to reciprocate within the hollow segment 65 in response to compressing pressure on the button 20 or expansion of spring 90. The final portion of the stem 84 is slidably carried in a lower continuous groove 96 in bottom enclosure wall 98.

Figure 6A:
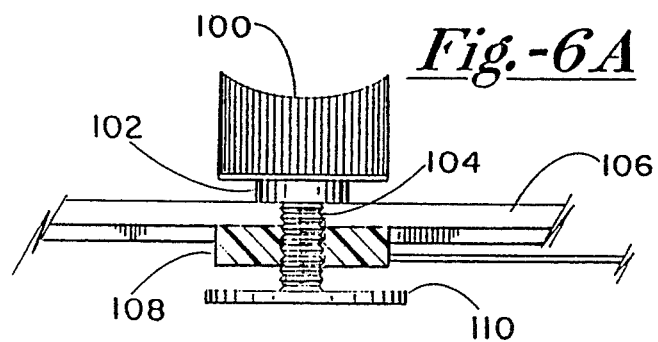
FIGS. 6A–6D are enlarged fragmentary details that depict an alternate draw wire control embodiment.
Figure 6B:
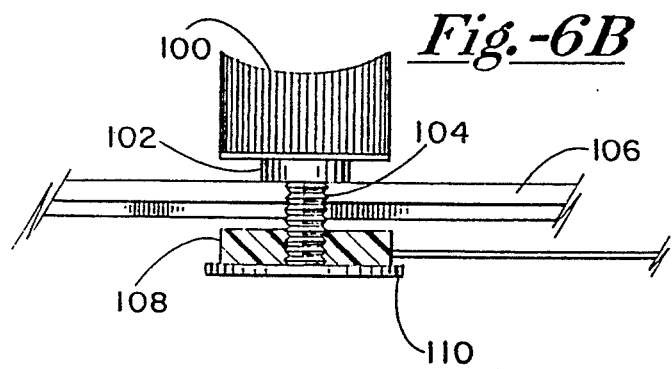
Figure 6C:
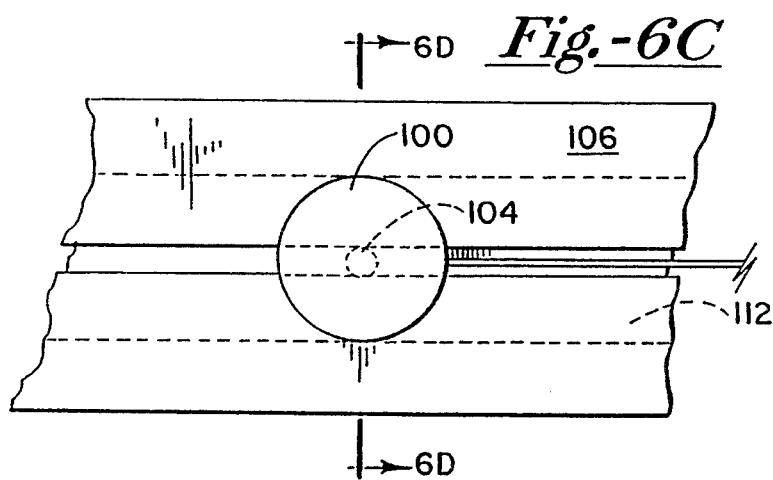
Figure 6D:
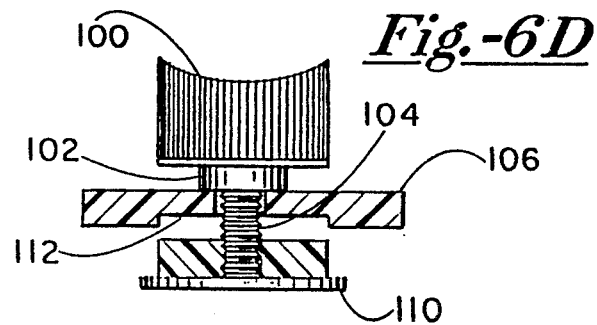

FIGS. 6A–6D show another alternate embodiment of a knob control for a tensioning wire that includes a button or hand-operated knurled knob 100 attached to a stem 102 which is attached to a threaded member 104 that proceeds through the top wall or shell 106 of the handle member, is threaded through a compression fitting or nut 108 and is fixed to a circular member or washer 110. A pull or draw wire 24 is seen attached to the member 108. As seen in FIGS. 6B and 6D, rotation of the knob or button 100 loosens or tightens the compression fitting 108 in a continuous slot 112 (FIG. 6D) allowing reciprocal adjustment of the button 100 as needed. This reciprocally adjusts the draw wire 24.

The system may be operated alone or with reciprocal sliding coordination of an inner modulating guide catheter. As stated above, the catheter section 14, of course, can be made with any desirable flexure resistance or Shore hardness and may be memoried to return to a predisposed position; but generally it is desirable that the catheter tube return to a straightened position when tension on the draw strings is relaxed.

Further embodiments of a handle appropriate for use with the catheter embodiments illustrated in FIGS. 1A, 1B, 2A and 2B are depicted in FIGS. 7A and 7B. These embodiments feature friction retained slidable thumb-operated knobs for the pull wires and may be used either for ablation or sheath-type catheter devices. In FIG. 7A, the handle is shown generally at 120 and includes a pair of thumb-operated longitudinally adjustable knob members 122 and 124 slidably mounted in respective slots 126 and 128 and attached to respective pull wires 130 and 132 which, along with internal catheter 134, extend through proximal main catheter tube 136. A sealed sheath access is shown at 138.

FIG. 7B shows a longitudinally aligned version of an ablation-type handle 140 in which thumb-operated knobs 142 and 144 are aligned longitudinally in a slot 146 controlling pull wires 148 and 150 which extends through an internal catheter 152 within main catheter 154. Electrical connection is accomplished through a conductor bundle represented by 156 and the jack-type plug-in connector is shown at 158.

An important aspect of the present invention is providing a catheter in which specific deflections or bends which provide specific shapes for diverse uses are readily achieved. An alternate embodiment of the highly maneuverable deflectable catheter of the invention which makes use of a further unique inner tubular deflection guide member is depicted in FIGS. 8, 9A–9C and 10.

FIG. 8 shows a flexible distal tip fragment of a highly deflectable ablation catheter with parts cut away and partially in section to show internal details. The catheter has a main or outer catheter tube 162 into which a series of longitudinally spaced cutouts or notches, as at 164, have been made. The catheter segment 162 may be manufactured using known catheter technology and materials much as that used in the catheter 14 in FIGS. 1A and 1B. Of course, any other suitable material or fabrication technique may be employed. The series of cutouts or notches 164 form an elongated deflection segment which extends proximally from a location close to distal electrodes as at ring electrode 166 and tip electrode 168. Flexure of the catheter 162 is controlled by one or more draw wires as at 172 anchored to the inner wall of the catheter 162 as at 170 and may extend throughout the length of the catheter and proceed through the lumen of an inner tube 174. An alternate routing of the draw wire is shown at 173.

In accordance with an important aspect of the embodiment of FIG. 8, the deflection of the catheter tube 162 is further modified and controlled by a longitudinally maneuverable or reciprocally operable hollow tubular catheter deflection guide member or shape control means 176 having one or more elongated cutout sections as at 178 or optionally it may be provided with weakened areas or be employed as a tube of constant flexure resistance. The tubular member 176 is slidably maneuverable within the lumen of outer catheter 162 in a manner which allows the cutout 178 or the distal tip to be disposed as desired with respect to the series of cutouts or notches 164 to control the flexure of the catheter 162. The system is designed so that the catheter 162 as directed or controlled by the tension or draw wire 172, 173 will bend preferably in the direction of the notches 164 as further modified by the location of the cutout 178. A sheath member or outer membrane 180 is further provided to cover the notches 164 and preserve the integrity of the internal catheter lumen from bodily fluids.

FIG. 12 is a view similar to that of FIG. 8 in which an axially adjustable (reciprocating) flexure filament or deflection shape wire control element 220 is used instead of (or possibly with) the inner tubular member 176. The member 220 may include one or more deflection segments 222 of reduced flexure resistance, i.e., reduced cross section or tensile, serially spaced by more rigid or larger diameter areas or segments 224. Optionally, the member may be a continuous rod member of constant diameter as shown by dashed lines 225. The member 220 may be threaded through an internal lumen or tube as at 226 along with other control members such as a control tension draw wire 172, 173. Of course, the electrical conductors are relatively fragile and must be routed separately from the control wires and deflection shape controls. The extended proximal portion 228 of the member 220 extends to a proximally external control handle and may be reciprocated in a manner similar to a control wire or the tube 176 of FIG. 8 to accomplish precise axial adjustment relative to the catheter body 162.

As shown in FIG. 12, sequential flexible and rigid aspects of the member 220 may be omnidirectional with respect to flexure direction preference. In this configuration, as with the embodiment of FIG. 8, the direction of flexure may be controlled by positioning one or more segments 222, 224 relative to weakened areas as cutouts 164 and employing element 172 to produce deflecting tension. As illustrated in FIG. 13, an asymmetric side wall 262 having a radially oriented relatively thin side wall portion 264, compared to the flexible but relatively more rigid side wall 266 including reinforcing filaments 268, may provide the weakened area for preferential catheter flexure or curvature.

Of course, the precise location of a bend or bends along the catheter can be controlled by the axial disposition of the one or more flexure points 222 within a given weakened catheter tip segment or possibly several such segments. In the case of the tube member 176 or the rod member 220, etc., of constant diameter, the controlled flexure of the catheter will occur adjacent the distal tip of the member 220. The relative length of the segments 222 and 224 also is a matter of design choice and will depend largely on the particular shape desired, examples of which are illustrated in FIGS. 9A–9C.

Of course, the member 220 may be a filament or wire in which the segments represented by 222 and 224 are segments of lesser and greater flexibility based on metallurgical or compositional considerations rather than dimensional diversity in a single composition. Also, for example, polymers or plastic materials of more or less flexibility, or the like, can be employed. The relative strength or flexibility may be made radially asymmetric or uni- or bi-directional if desired to itself help control the catheter shape.

It should also be recognized that all the cooperating members or elements of the shape control system are flexible and that control is achieved by alignment of relative differences in rigidity or flexibility among the elements to enable desired shapes to be produced. This involves the catheter tube 46, 162, e.g., at the tube 176, member 220 or other flexure modulating member in view of the placement of tensioning control members as at 56, 172, etc.

Control can be achieved in accordance with the invention even using a standard flexible or even floppy distal catheter section of constant rigidity with one or more wall-anchored tensioning control members modulating the flexure including the point or points of curvature by the axial adjustment (reciprocation) of the distal tip of a deflection shape control or modulation device or to align one or more areas of added flexibility if desired and using the draw or tensioning wires to create the desired shaping to produce any desired point or points of and degree of curvature. Placement of the cooperating elements can be noted and repeated to duplicate shape as desired.

As mentioned above, the axial positioning (reciprocal movement) of the member 220 may be accomplished by any of several types of reciprocating means attached to the proximal section 228, which itself may extend throughout the length of the catheter to an operating handle control as exemplified in the FIGS. 3A–7B. Tip control is based on a coordination of the axial alignment of the desired one or more flexible segments 222 at the desired location relative to the catheter 162, 262. An elongate, relatively rigid internal tube as at 176 without weakened areas may also be used in conjunction with the member 220 to mask one or more proximal flexible sections 222 so that only those more distal (extending beyond the tube) will flex. In any event, once the proper alignment is achieved, flexure is readily accomplished by operating draw wires.

FIGS. 9A–9C depict schematically a few examples of the various flexure shapes of the catheter 162 in conjunction with the use of an inner tubular deflection guide member 176 or the shaft or wire member 220. FIG. 9A depicts how the system deflects with the tubular member 176 withdrawn proximal of the notches 164 so that the tension in the draw wire 172 products a continuous arcuate curve 190 in the distal tip of the catheter 162. FIG. 9B depicts a situation in which a few of the notches 164 at the catheter tip are beyond the end of inner tubular member 176 or wire or shaft member 220 and so catheter flexure at that point is not restricted. This produces a bend or flexure at 192 and a further flexure at 194 based on the location of the cutout 178 or flexible segment 222. FIG. 9C discloses a disposition in which the only flexure is produced by the cutout 178 or flexible segment 222 at 196.

It can readily be seen that embodiments exemplified by FIGS. 8 and 12 lend themselves to applications in which real time shape adjustments are required in the distal catheter tip to provide certain specialized functions. The inner catheter control or deflection guide tube 176, or member 220, can be configured in any manner with respect to number, size and angular disposition of cutouts to produce a desired flexure shape in the outer catheter 162.

It should further be noted that the weakened or articulated section or sections of preferred flexure in the catheter wall may be made any length in any particularly embodied form. The purpose, of course, is to enable the user to place the one or more ablation and/or recording electrodes in a position to address any specific location in a cardiac chamber or valve surface. Unusual shapes are particularly necessary to address those areas difficult to continually contact using earlier shape control techniques. It must be remembered that the catheter must have the ability to place an electrode system in sustained contact with tissue that is essentially constantly in motion, as is the case within a beating heart. While distal electrodes 166 and 168 are illustrated, it will further be understood that any desirable size, spacing and number of recording and/or ablation electrodes can be used.

Figure 10:
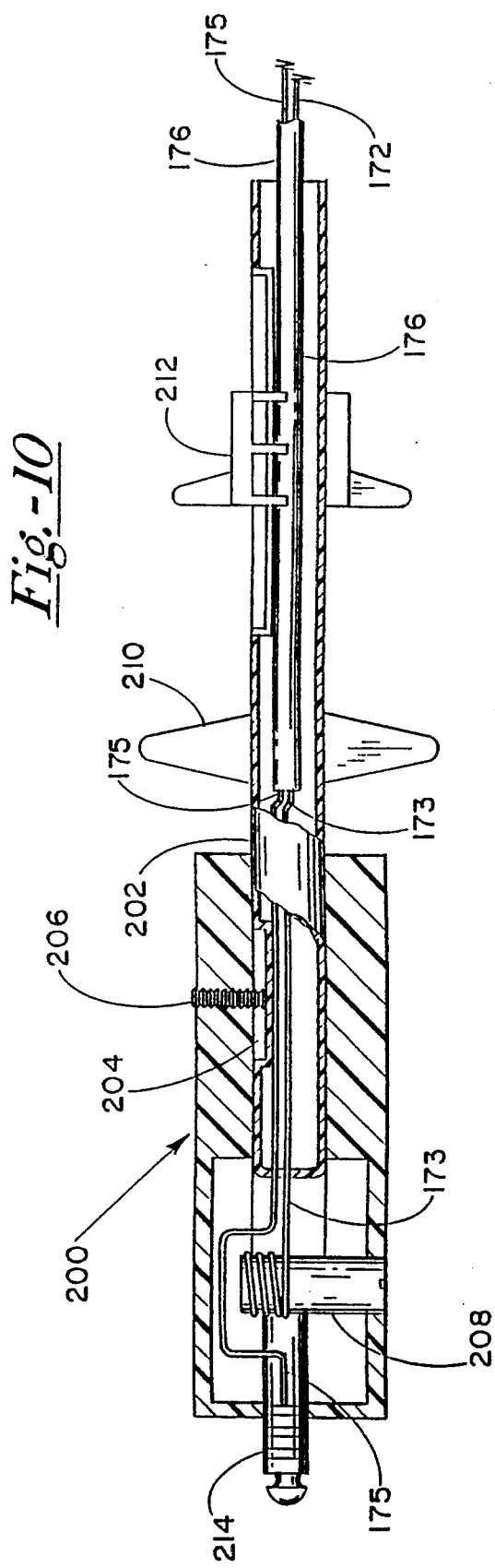
FIG. 10 depicts a handle for use with the catheter of FIG. 8.

FIG. 10 exemplifies a handle for use with the embodiment of the catheter depicted in FIGS. 8 and 12. It includes a handle shown generally at 200 in which the proximal end of the main catheter 202 is reciprocally displaceable within the handle over the length of a slot or key way 204 which cooperates with a set screw 206 to adjust the longitudinal position of the catheter 202.

The deflection draw or tension wire 173 is threaded through deflection guide member 176 (or tube 226, FIG. 12) and the proximal end thereof is fixed to a member 208 which may be a threadably engaged tension adjusting screw in which the tension can initially be adjusted during assembly of the handle. A further hand-operated longitudinal catheter finger-operated displacement handle is shown at 210 which can be used to reciprocally adjust the position of the catheter which thereby modulates the tension of the draw wire 173 on the distal end of the catheter system thereby controlling the flexure of the tip.

A further finger-operated reciprocating or inner deflection guide tube positioning device 212 is shown attached to the internal catheter 176 (but may also be attached to the proximal lead 228 of the member 220) and is used to slidably adjust the position of the internal tubular catheter 176 (or member 220) to properly position the one or more cutouts 178 (FIG. 8) (or flexible segments 222) as desired to produce the proper deflection pattern in the catheter 162 (FIGS. 8 and 12). Electrical connector 175 is shown connected so as to be independent of the reciprocal motion of the catheter cylinder 202 so that during the operation of the system no tension is put on the electrical conductor which is shown connected to jack-type plug-in member 214.

This invention has been described herein in considerable detail in order to comply with the Patent Statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

What is claimed is:

1. A deflection system for precisely controlling the shape of a distal catheter section, including a flexible distal working catheter area, of a tubular vascular catheter comprising:
   (a) a distal catheter section having an outer wall, a distal end, and a proximal end and including a distal working tip area, the shape of which is sought to be controlled;
   (b) a plurality of relatively weaker or more flexible wall areas aligned in radially diverse directions serially spaced for producing greater flexibility in a preferred direction in the outer wall of the distal catheter section proximally spaced from the distal end of the distal section, each weaker wall area producing a tendency for the catheter to bend preferentially in the direction of and in the vicinity of the weaker wall segment; and
   (c) flexure control means including reciprocally operable means for applying an adjustable tension or pulling force to the distal catheter section from distal of the weaker wall area in a manner that produces curvature of the catheter at the one or more weaker wall areas in the desired direction of and in the vicinity of the weaker wall areas.

2. The apparatus of claim 1 further comprising a plurality of sequential weaker wall areas aligned in radially diverse directions.

3. The apparatus of claim 1 wherein the weaker wall areas include cutouts.

4. The apparatus of claim 1 wherein the one or more relatively weaker wall areas are characterized by radially directionally oriented reduced wall thickness.

5. The apparatus of claim 3 further comprising flexible outer covering sheath means over the cutouts to preserve the liquid-tight integrity of the distal section of the catheter.

6. The apparatus of claim 1 wherein the flexure control means comprises one or more tensioning pull wires.

7. The apparatus of claim 1 wherein the flexure control means further includes a handle means having at least one hand operable reciprocally adjustable knob means connected to move each reciprocally operable means to thereby modulate the deflection of the catheter tip.

8. The apparatus of claim 7 wherein the at least one hand operable reciprocally adjustable knob means operates along a series of spaced predetermined fixed positions and further comprises retaining spring means to retain the knob means in the desired fixed position.

9. The apparatus of claim 7 wherein the at least one hand operable reciprocally adjustable knob means is slidably mounted in a groove.

10. A deflection system for precisely controlling the shape of a distal catheter section, including a flexible distal working catheter area, of a tubular vascular catheter comprising:
    (a) a distal catheter section having an outer wall, a distal end, and a proximal end and including a distal working tip area, the shape of which is sought to be controlled;
    (b) a plurality of serially spaced, relatively weaker or more flexible wall areas for producing greater flexibility in a preferred direction in the outer wall of the distal catheter section proximally spaced from the distal end of the distal section, each weaker or more flexible wall area producing a tendency for the catheter to bend preferentially in the direction of and in the vicinity of the weaker wall segment; and
    (c) flexure control means including a plurality of reciprocally operable means for applying an adjustable tension or pulling force to the distal catheter section and wherein each said reciprocally operable means is attached to the catheter wall at a location distal a different one of said weaker or more flexible wall areas in a manner that produces curvature of the catheter at the one or more weaker wall areas in the desired direction of and in the vicinity of the weaker wall areas.

11. The apparatus of claim 10 wherein the weaker wall areas include cutouts.

12. The apparatus of claim 10 wherein the one or more relatively weaker wall areas are characterized by radially directionally oriented reduced wall thickness.

13. The apparatus of claim 10 wherein the flexure control means comprises:
    (a) a plurality of reciprocally operable control wires, one anchored just distal of each more flexible segment; and
    (b) means for controlling reciprocal motion of each such control wire.

14. The apparatus of claim 13 wherein the means for controlling reciprocal motion of each control wire further includes a handle means having a plurality of individually hand operable reciprocally adjustable knob means each of which is connected to reciprocally move a respective control wire for applying and modulating the deflection of the catheter tip.

15. The apparatus of claim 14 wherein the at least one hand operable reciprocally adjustable knob means operates along a series of spaced predetermined fixed positions and further comprises retaining spring means to retain the knob means in the desired fixed position.

16. The apparatus of claim 14 wherein the at least one hand operable reciprocally adjustable knob means is slidably mounted in a groove.

17. A method of controlling the shape of a distal catheter section comprising the steps of:
(a) providing a distal catheter section having one or more weakened wall segments proximally spaced from the distal end thereof, one of more reciprocating tension control members including reciprocally operating means for applying a longitudinal force to the distal section of the catheter, said tension control members being secured distal of the weakened wall segments and slidably adjustable deflection shape control means reciprocally slidably disposed in said distal catheter section;
(b) slidably adjusting said deflection control means as desired along the distal catheter section; and
(c) using said reciprocally operating means to operate said tension control members to cause deflection of said distal catheter section at locations in accordance with the location of said slidably adjustable deflection shape control means and said tension control members.

18. A deflection system for controlling the shape of a distal catheter section, including a working distal catheter area, of a tubular catheter comprising:
(a) a distal catheter section of a desired flexibility, having an outer wall, a distal end, and a proximal end and including a working distal area, the shape of which is sought to be controlled;
(b) flexure control means including reciprocally operable means for applying an adjustable tension or pulling force to the distal catheter section at one or more attachment locations in the outer wall segments in a manner that produces curvature of the distal catheter section proximal a corresponding attachment location in the direction of the force;
(c) adjustable deflection shape control means disposed in said distal catheter section and reciprocally slidable therein to cooperate with the distal catheter section and said flexure control means to modulate the shape assumed by the distal catheter section; and
(d) wherein the adjustable deflection shape control means comprises a flexible elongated hollow member.

19. The apparatus of claim 18 wherein the adjustable deflection shape control means comprises an elongated solid member operated in combination with said elongated hollow member.

20. The apparatus of claim 18 further comprising one or more recording/ablation electrode means on said working catheter area.

21. The apparatus of claim 18 wherein the adjustable deflection shape control means comprises an elongated hollow member having one or more spaced areas of greater flexibility.

22. The apparatus of claim 18 wherein the adjustable deflection shape control means comprises an hollow tubular member with parts removed from the side wall thereof to create said segments of directionally preferred greater flexibility.

23. A controlled deflection system for precisely controlling the shape of a distal catheter section, including a distal working catheter area, of a tubular vascular catheter comprising:
(a) a distal catheter section having an outer wall, a distal end, and a proximal end and including a distal working area, the shape of which is sought to be controlled;
(b) one or more serially spaced, relatively weaker or more flexible wall areas for inducing greater flexibility in a preferred direction in such outer wall of the distal catheter section proximally spaced from the distal end thereof, each weaker wall area producing a preferential tendency for the catheter to bend in the direction and in the location of the weaker wall area;
(c) flexure control means including reciprocally operable means for applying an adjustable longitudinal force to the distal catheter section from distal of the weaker wall areas in a manner that produces curvature of the catheter at the locations of the one or more weaker areas in the preferred direction; and
(d) adjustable deflection shape control means disposed in said distal catheter section and reciprocally slidable therein to cooperate with said one or more weaker wall areas and said flexure control means to modulate the shape assumed by the distal catheter section.

24. The apparatus of claim 23 further comprising a plurality of weaker wall areas and wherein said flexure control means comprises a plurality of reciprocally operable means and wherein each said reciprocally operable means is attached to the wall of the catheter at a location distal a different one of said weaker wall areas.

25. The apparatus of claim 23 further comprising a plurality of sequential relatively weaker wall areas aligned in radially diverse directions.

26. The apparatus of claim 24 further comprising a plurality of sequential weaker wall areas aligned in radially diverse directions.

27. The apparatus of claim 23 wherein the relatively weaker wall areas include cutouts.

28. The apparatus of claim 26 wherein the relatively weaker wall areas include cutouts.

29. The apparatus of claim 23 wherein the one or more relatively weaker wall areas are characterized by radially directionally oriented reduced wall thickness.

30. The apparatus of claim 25 wherein the one or more relatively weaker wall areas are characterized by radially directionally oriented reduced wall thickness.

31. The apparatus of claim 27 further comprising protective flexible outer covering sheath means over the cutouts to preserve the liquid-tight integrity of the distal section of the catheter.

32. The apparatus of claim 23 wherein the adjustable deflection shape control means comprises an elongated flexible solid member.

33. The apparatus of claim 23 wherein the adjustable deflection shape control means comprises an elongated flexible solid member having one or more spaced segments of reduced rigidity.

34. The apparatus of claim 33 wherein the adjustable deflection shape control means is a wire or rod having one or more segments of reduced diameter.

35. The apparatus of claim 23 wherein the adjustable deflection shape control means comprises a flexible elongated hollow member.

36. The apparatus of claim 23 wherein the adjustable deflection shape control means comprises an elongated hollow member having one or more spaced areas of greater flexibility.

37. The apparatus of claim 23 wherein the adjustable deflection shape control means comprises an hollow tubular member with parts removed from the side wall thereof to create said segments of directionally preferred greater flexibility.

38. The apparatus of claim 23 wherein the adjustable deflection shape control means comprises an elongated solid member operated in combination with an elongated hollow member.

39. The apparatus of claim 23 further comprising one or more recording/ablation electrode means on said working catheter area.

40. The apparatus of claim 23 further comprising one or more recording/ablation electrode means on said working catheter area.

41. A deflection system for controlling the shape of a distal catheter section, including a working distal catheter area, of a tubular catheter comprising:
  (a) a distal catheter section of a desired flexibility, having an outer wall, a distal end, and a proximal end and including a working distal area, the shape of which is sought to be controlled;
  (b) flexure control means including reciprocally operable means for applying an adjustable tension or pulling force to the distal catheter section at one or more attachment locations in the outer wall segments in a manner that produces curvature of the distal catheter section proximal a corresponding attachment location in the direction of the force;
  (c) adjustable deflection shape control means disposed in said distal catheter section and reciprocally slidable therein to cooperate with the distal catheter section and said flexure control means to modulate the shape assumed by the distal catheter section; and
  (d) wherein the adjustable deflection shape control means comprises an elongated flexible solid member having one or more spaced segments of greater flexibility.

42. The apparatus of claim 41 wherein the adjustable deflection shape control means is a wire or rod having one or more segments of reduced diameter.

43. The apparatus of claim 42 wherein the areas of greater flexibility are directionally oriented.

44. The apparatus of claim 41 further comprising one or more recording/ablation electrode means on said working catheter area.

45. The apparatus of claim 41 wherein the flexure control means further includes a handle means having at least one hand operable reciprocally adjustable knob means connected to move each reciprocally operable means to thereby modulate the deflection of the catheter tip.

46. The apparatus of claim 45 wherein the at least one hand operable reciprocally adjustable knob means operates along a series of spaced predetermined fixed positions and further comprises retaining spring means to retain the knob means in the desired fixed position.

47. The apparatus of claim 45 wherein the at least one hand operable reciprocally adjustable knob means is slidably mounted in a groove.

48. The apparatus of claim 41 wherein the flexure control means comprises:
  (a) a plurality of reciprocally operable control wires; and
  (b) means for controlling reciprocal motion of each such control wire.

49. The apparatus of claim 48 wherein the means for controlling reciprocal motion of each control wire further includes a handle means having a plurality of individually hand operable reciprocally adjustable knob means each of which is connected to reciprocally move a respective control wire for applying and modulating the deflection of the catheter tip.

50. The apparatus of claim 48 wherein the at least one hand operable reciprocally adjustable knob means operates along a series of spaced predetermined fixed positions and further comprises retaining spring means to retain the knob means in the desired fixed position.

51. The apparatus of claim 48 wherein the at least one hand operable reciprocally adjustable knob means is slidably mounted in a groove.

52. A precisely controlled distal catheter section for a vascular catheter comprising:
  (a) an hollow elongated tubular distal working catheter section having a distal end and a proximal end, an outer wall and describing at least a main internal lumen;
  (b) one or more serially spaced, relatively weaker or more flexible wall areas in said outer wall of the distal catheter section proximately spaced from the distal end thereof;
  (c) tension control means for applying longitudinal force to the distal section of the catheter from distal of the one or more weakened areas in a manner that encourages bending thereof in the direction of the weakened areas;
  (d) deflection shape control means disposed in said distal catheter section and reciprocally slidable therein to modulate cooperation between said one or more weakened wall areas and said tension control means to modulate the shape assumed by the distal catheter section; and
  (e) handle means having at least one hand operable reciprocally adjustable knob means connected to reciprocally adjust each tension control means and adjustable knob means connected to reciprocally adjust the shape control means of the catheter to modulate the locations and amounts of deflection of the catheter.

53. The apparatus of claim 52 wherein each knob means operates along a series of spaced predetermined fixed positions and further comprises means to retain the knob means in the desired fixed position.

54. The apparatus of claim 52 wherein the adjustable deflection shape control means further comprises an elongated hollow member having one or more spaced segments of greater flexibility.

55. The apparatus of claim 52 wherein the adjustable deflection shape control means is a wire or rod having segments of different diameters.

56. The apparatus of claim 52 wherein the deflection shape control means is a tube member with one or more spaced weakened segments that slidably reciprocates outside the working catheter.

57. A shape control system for controlling the flexure shape of the distal section of a flexible tubular vascular catheter comprising:
  (a) a flexible main tubular catheter having a distal end and a proximal end, a distal working section, the deployed shape of which is sought to be controlled, and describing a continuous internal primary lumen;

(b) one or more bending areas of directionally preferred greater flexibility proximally spaced from the distal end of the distal section of the main catheter;

(c) flexure control means including one or more tension members for applying longitudinal force to the distal section of the catheter from distal of one or more bending areas of the deflection segment in a manner that produces bending of the deflection segment in the preferred direction of each bending area;

(d) a flexible deflection shape control member selected from hollow tubes and solid rods comprising an inner tubular deflection guide member disposed in the primary lumen of the catheter and configured to be reciprocally slidable therein, the deflection shape control member itself being provided with one or more sections of greater flexibility, in the form of areas that encourage the catheter to bend at locations where the more flexible segments of the shape control member align with the bending areas of the catheter;

(e) deflection guide control means for the reciprocal adjustment of the deflection shape control member; and (f) wherein relative alignment of the one or more weakened sections of the deflection shape control member by slidable adjustment of the deflection shape control member may be used to modify the bending of the main catheter.

58. The apparatus of claim 57 wherein the flexure control means comprises:

(a) one or more reciprocally operable control wires, anchored just distal of the deflection segment in the outer catheter;

(b) means for controlling reciprocal motion of the control wire; and (c) wherein the deflection shape control member comprises finger-operated control means for reciprocal adjustment of the deflection shape control member attached to the deflection shape control member.

59. The apparatus of claim 58 wherein the means for controlling reciprocal motion of the control wire(s) further includes a handle means having hand operable reciprocally adjustable knob means connected to the control wire for controlling reciprocal motion of the control wire operable to modulate the longitudinal force applied to the distal section of the catheter.

60. The apparatus of claim 58 wherein the at least one hand operable reciprocally adjustable knob means operates along a series of spaced predetermined fixed positions and further comprises retaining spring means to retain the knob means in the desired fixed position.

61. The apparatus of claim 58 wherein the at least one hand operable reciprocally adjustable knob means is slidably mounted in a groove.

* * * * *